ional Search Report (Form PCT/ISA/210)", dated Jan. 3,

United States Patent
Hong et al.

(10) Patent No.: US 10,392,328 B2
(45) Date of Patent: Aug. 27, 2019

(54) LOW-CARBON ENVIRONMENTALLY-FRIENDLY FOAMER COMPOSITION

(71) Applicant: Zhejiang Quhua Fluor-Chemistry Co Ltd, Zhejiang (CN)

(72) Inventors: Jiangyong Hong, Zhejiang (CN); Bo Yang, Zhejiang (CN); Yang Zhao, Zhejiang (CN); Yan Zhang, Zhejiang (CN); Huadong Zhou, Zhejiang (CN); Hao Ouyang, Zhejiang (CN); Haitao Gong, Zhejiang (CN); Min Fang, Zhejiang (CN)

(73) Assignee: Zhejiang Quhua Fluor-Chemistry Co Ltd, Zhejiang (CN)

( * ) Notice: Subject to any disclaimer, the term of this patent is extended or adjusted under 35 U.S.C. 154(b) by 0 days.

(21) Appl. No.: 16/076,324

(22) PCT Filed: Jul. 21, 2017

(86) PCT No.: PCT/CN2017/000461
§ 371 (c)(1),
(2) Date: Aug. 8, 2018

(87) PCT Pub. No.: WO2018/120258
PCT Pub. Date: Jul. 5, 2018

(65) Prior Publication Data
US 2019/0039976 A1 Feb. 7, 2019

(30) Foreign Application Priority Data
Dec. 26, 2016 (CN) .......................... 2016 1 1217438

(51) Int. Cl.
| | |
|---|---|
| *C07C 21/18* | (2006.01) |
| *C07C 19/08* | (2006.01) |
| *C08L 75/04* | (2006.01) |
| *C08J 9/14* | (2006.01) |
| *C08G 101/00* | (2006.01) |

(52) U.S. Cl.
CPC .............. *C07C 21/18* (2013.01); *C07C 19/08* (2013.01); *C08J 9/144* (2013.01); *C08J 9/146* (2013.01); *C08L 75/04* (2013.01); *C08G 2101/00* (2013.01); *C08J 2203/142* (2013.01); *C08J 2203/162* (2013.01); *C08J 2203/202* (2013.01); *C08L 2203/14* (2013.01)

(58) Field of Classification Search
None
See application file for complete search history.

(56) References Cited

U.S. PATENT DOCUMENTS

2016/0311735 A1  10/2016  Wang et al.

FOREIGN PATENT DOCUMENTS

| CN | 1756793 | 4/2006 |
|---|---|---|
| CN | 102300975 | 12/2011 |
| CN | 102574756 | 7/2012 |
| CN | 102686957 | 9/2012 |
| CN | 105829270 | 8/2016 |
| CN | 106750488 | 5/2017 |
| WO | WO-2015092211 A1 * | 6/2015 ........... C07C 17/383 |

OTHER PUBLICATIONS

WO2015092211, English translation, Jun. 25, 2015, pp. 1-33 (Year: 2015).*
"International Search Report (Form PCT/ISA/210)", dated Jan. 3, 2018, with English translation thereof, pp. 1-5.

* cited by examiner

*Primary Examiner* — Medhanit W Bahta
(74) *Attorney, Agent, or Firm* — JCIPRNET

(57) ABSTRACT

A low-carbon environmentally-friendly foamer composition is disclosed. The composition includes the following ingredients in mass percentage: 60-98.99% of 1-chloro-3,3,3-trifluoropropene, 1-39.9% of 1,1,1,2,3-pentafluoropropane and 0.01-1% of 1,2,2,3-tetrafluoropropane. The GWP value of the low-carbon environmentally-friendly foamer composition is smaller than the GWP value of a single-medium HFC-245fa. This low-carbon environmentally-friendly foamer composition has the features of environmental protection, excellent foaming performance and little modification of foaming devices, and can reduce the heat conductivity coefficient and overall energy consumption level. Therefore, the low-carbon environmentally-friendly foamer composition is the best choice for high-performance hard insulating foam, and is an ideal choice of future foamer.

10 Claims, No Drawings

LOW-CARBON ENVIRONMENTALLY-FRIENDLY FOAMER COMPOSITION

CROSS-REFERENCE TO RELATED APPLICATION

This application is a 371 of international application of PCT application serial no. PCT/CN2017/000461, filed on Jul. 21, 2017, which claims the priority benefit of China application no. 201611217438.0, filed on Dec. 26, 2016. The entirety of each of the above-mentioned patent applications is hereby incorporated by reference herein and made a part of this specification.

BACKGROUND

1. Field of the Invention

This invention relates to the application field of foamer, in particular to a low-carbon environmentally-friendly foamer composition.

2. Description of Related Art

At present, foamer systems replacing HCFC-141b in the household industry (including refrigerators, freezers, and water heaters) mainly include cyclopentane, HFC-245fa, HFC-245fa/cyclopentane, and a small amount of R-134a, 365mfc and all-water foaming systems, which have advantages and disadvantages respectively. The physical performance of different foamer directly affects the performance of the final foam products. HFC-245fa has a GWP value of 790, is incombustible, and does not need investment in anti-explosion equipment. Foam products of HFC-245fa have a smaller heat conductivity coefficient, higher mobility, and higher strength and dimensional stability, but have a relatively high GWP value. Also, HFC-245fa will be certainly gradually replaced in the future because of increasingly strict environmental protection requirements in the world.

HFO-1233zd is usually deemed to have an ODP value of about 0 and a GWP value of 1, is incombustible and low in toxicity, does not need an anti-explosion device during the foaming process, and has a boiling point of 19° C. which is close to room temperature. HFO-1233zd is conveniently operated, can be directly used on an HFC-245fa foaming device, and is well compatible with polyols. HFO-1233zd has low gas-phase heat conductivity, and the foam thereof has high heat insulation performance. At present, large companies in the world are strongly promoting HFO-1233zd in the polyurethane foam industry. HFO-1233zd is a new-generation foamer capable of meeting the requirements of various processes and environmental protection requirements. HFO-1233zd has features of high efficiency, energy conservation, incombustibility, no volatile organics, low GWP, safety, and environmental-friendless. However, cells generated by HFO-1233zd alone also have certain defects. Therefore, HFO-1233zd is usually used in combination with other ingredients.

For example, in Chinese Patent No. CN102300975A, published on Dec. 28, 2011 and titled with "Azeotrope-like composition of Perfluoropropane, Chlorotrifluoropropylene and Hydrogen Fluoride", a ternary composition and a method for preparing the azeotrope-like composition is disclosed. Ratios, temperatures, and pressures of all azeotrope-like compositions of various ingredients are provided.

For another example, in Chinese Patent No. CN1756793A, published on Apr. 5, 2006 and titled with "Hydrofluorocarbon composition", a composition including 1,1,1,3,3-pentafluorobutane (HFC-365mfc) and 1,1,1,3,3-pentafluoropropane (HFC-245fa) is disclosed, wherein the weight ratio of the HFC-365mfc to HFC-245fa is 60:40-75:25. Such composition is applied to the polyurethane foam field.

For another example, Chinese Patent No. CN102574756A is published on Jul. 11, 2012 and titled with "Composite of Azeotropic Mixtures and Azeotropic-like Mixtures of 1-Chloro-3,3,3-Trifluoropropene and HFC-245eb". The invention relates to a composition including azeotropic mixtures and azeotropic-like mixtures of 1-Chloro-3,3,3-trifluoropropene (HCFO-1233zd) and 1,1,1,2,3-perfluoropropane (HFC-245eb) and applications thereof.

The foamer compositions disclosed in the above patents have defects, such as high GWP value, large heat conductivity coefficient, or high energy consumption of the whole machine during use. Therefore, there is a need to develop a foamer composition with higher foaming performance and environmentally-friendly performance.

SUMMARY

The objective of this invention is to provide an environmentally-friendly foamer composition with a low GWP value, a small heat conductivity coefficient and low energy consumption so as to overcome the defects in the prior art.

In order to solve the above technical problems, this invention adopts the following technical solution: A low-carbon environmentally-friendly foamer composition includes the following ingredients in mass percentage:

| | |
|---|---|
| 1-chloro-3,3,3-trifluoropropene | 60-98.99% |
| 1,1,1,2,3-pentafluoropropane | 1-39.9% |
| 1,2,2,3-tetrafluoropropane | 0.01-1%. |

The low-carbon environmentally-friendly foamer composition of this invention preferably includes the following ingredients in mass percentage:

| | |
|---|---|
| 1-chloro-3,3,3-trifluoropropene | 69.99-94.99% |
| 1,1,1,2,3-pentafluoropropane | 5-30% |
| 1,2,2,3-tetrafluoropropane | 0.01-1%. |

The low-carbon environmentally-friendly foamer composition of this invention preferably includes the following ingredients in mass percentage:

| | |
|---|---|
| 1-chloro-3,3,3-trifluoropropene | 80-89.99% |
| 1,1,1,2,3-pentafluoropropane | 10-19.9% |
| 1,2,2,3-tetrafluoropropane | 0.01-1%. |

The low-carbon environmentally-friendly foamer composition of this invention preferably includes the following ingredients in mass percentage:

| | |
|---|---|
| 1-chloro-3,3,3-trifluoropropene | 85-89.99% |
| 1,1,1,2,3-pentafluoropropane | 10-14.99% |
| 1,2,2,3-tetrafluoropropane | 0.01-1%. |

Preferably, the low-carbon environmentally-friendly foamer composition of this invention has a boiling point of 18-19° C. at the pressure of 101.3 KPa.

This invention also discloses a preparation method for the composition. The preparation method includes physically mixing the ingredients by respective mass percentage in the liquid phase state to obtain the low-carbon environmentally-friendly foamer composition.

1-Chloro-3,3,3-trifluoropropene (HFO-1233zd) is usually deemed to have an ODP value of about 0 and a GWP value of 1, is incombustible and low in toxicity, does not need an anti-explosion device during the foaming process, and has a boiling point of 19° C., which is close to room temperature. HFO-1233zd is conveniently operated, can be directly used on an HFC-245fa foaming device, and is well compatible with polyols. HFO-1233zd has low gas-phase heat conductivity, and the foam thereof has high heat insulation performance. However, cells generated by HFO-1233zd alone also have certain defects.

1,1,1,2,3-Perfluoropropane (HFC-245eb) has a boiling point of 23° C., is incombustible, and does not need investments in anti-explosion equipment. Foam products of HFC-245eb have a lower heat conductivity coefficient, higher mobility, and higher strength and size stability. With a 290 GWP value, HFC-245eb serves as an intermediate for synthesizing a new environmentally-friendly fourth-generation refrigerant.

1,2,2,3-Tetrafluoropropane (HFC-254ca) has a boiling point of 26° C., is incombustible, and does not need investments in anti-explosion equipment. Foam products of HFC-254ca have a smaller heat conductivity coefficient, higher mobility, and high strength and dimensional stability.

The foamer composition of this invention applies to the polyurethane foam industry. Compared with existing foamer systems (HFC-245fa and cyclopentane) of the same model, the heat conductivity coefficient of refrigerators using the foamer composition of this invention is respectively reduced by 5-50% (in comparison with an HFC-245fa system) and 5-30% (in comparison with a cyclopentane system) in a refrigerator.

The foamer composition of this invention applies to the polyurethane foam industry. Compared with existing foamer systems (HFC-245fa and cyclopentane) of the same model, the overall energy consumption of refrigerators using the foamer composition of this invention is respectively reduced by 2-35% (in comparison with an HFC-245fa system) and 3-55% (in comparison with a cyclopentane system) in a refrigerator.

Compared with the prior art, this invention has the following advantages:

1. Low GWP value: relative to the single-medium HFC-245fa, the GWP value of the foamer composition of this invention is greatly reduced.

2. Small heat conductivity coefficient: the foamer composition of this invention can obviously reduce the heat conductivity coefficient. When the foamer composition of this invention is applied to refrigerators, the heat conductivity is reduced by 12.5-42.8% (in comparison with an HFC-245fa system), 9.4-25.9% (in comparison with a cyclopentane system), and 0.4-15.9% (compared with both HFO-1233zd and HFC-245eb mixture systems without HFC-254ca).

3. Low energy consumption: the foamer composition of this invention can obviously reduce energy consumption. When the foamer composition of this invention is applied to refrigerators, the energy consumption is reduced by 13.8-32.3% (in comparison with an HFC-245fa system), 14-50.2% (in comparison with a cyclopentane system), and 8.9-24.8% (compared with both HFO-1233zd and HFC-245eb mixture systems without HFC-254ca).

DESCRIPTION OF THE EMBODIMENTS

The contents of this invention are described in further detail through the following embodiments, but this invention is not limited to the following embodiments.

Embodiment 1

600 g of HFO-1233zd, 399 g of HFC-245eb and 1 g of HFC-254ca were mixed in liquid phase state in a steel cylinder to obtain a low-carbon environmentally-friendly foamer composition; the mass percentage of HFO-1233zd was 60%; the mass percentage of HFC-245eb was 39.9%; and the mass percentage of HFC-254ca was 0.1%. The performance of the low-carbon environmentally-friendly foamer composition was tested, and the test results can be seen in Tables 1-3, wherein the boiling point of the low-carbon environmentally-friendly foamer composition was 18.3° C. at the pressure of 101.3 KPa.

Embodiment 2

989.9 g of HFO-1233zd, 10 g of HFC-245eb, and 0.1 g of HFC-254ca were mixed in liquid phase state in a steel cylinder to obtain a low-carbon environmentally-friendly foamer composition; the mass percentage of HFO-1233zd was 98.99%; the mass percentage of HFC-245eb was 1%; and the mass percentage of HFC-254ca was 0.01%. The performance of the low-carbon environmentally-friendly foamer composition was tested, and the test results can be seen in Tables 1-3, wherein the boiling point of the low-carbon environmentally-friendly foamer composition was 18.9° C. at the pressure of 101.3 KPa.

Embodiment 3

699 g of HFO-1233zd, 300 g of HFC-245eb and 1 g of HFC-254ca were mixed in liquid phase state in a steel cylinder to obtain a low-carbon environmentally-friendly foamer composition; the mass percentage of HFO-1233zd was 69.9%; the mass percentage of HFC-245eb was 30%; and the mass percentage of HFC-254ca was 0.1%. The performance of the low-carbon environmentally-friendly foamer composition was tested, and the test results can be seen in Tables 1-3, wherein the boiling point of the low-carbon environmentally-friendly foamer composition was 18.5° C. at the pressure of 101.3 KPa.

Embodiment 4

799 g of HFO-1233zd, 200 g of HFC-245eb and 1 g of HFC-254ca were mixed in their liquid phase state in a steel cylinder to obtain a low-carbon environmentally-friendly foamer composition; the mass percentage of HFO-1233zd was 79.9%; the mass percentage of HFC-245eb was 20%; and the mass percentage of HFC-254ca was 0.1%. The performance of the low-carbon environmentally-friendly foamer composition was tested, and the test results can be seen in Tables 1-3, wherein the boiling point of the low-carbon environmentally-friendly foamer composition was 18.6° C. at the pressure of 101.3 KPa.

Embodiment 5

849 g of HFO-1233zd, 150 g of HFC-245eb and 1 g of HFC-254ca were mixed in their liquid phase state in a steel cylinder to obtain a low-carbon environmentally-friendly foamer composition; the mass percentage of HFO-1233zd was 84.9%; the mass percentage of HFC-245eb was 15%; and the mass percentage of HFC-254ca was 0.1%. The performance of the low-carbon environmentally-friendly foamer composition was tested, and the test results can be seen in Tables 1-3, wherein the boiling point of the low-carbon environmentally-friendly foamer composition was 18.7° C. at the pressure of 101.3 KPa.

Embodiment 6

890 g of HFO-1233zd, 100 g of HFC-245eb and 10 g of HFC-254ca were mixed in their liquid phase state in a steel cylinder to obtain a low-carbon environmentally-friendly foamer composition; the mass percentage of HFO-1233zd was 89%; the mass percentage of HFC-245eb was 10%; and the mass percentage of HFC-254ca was 1%. The performance of the low-carbon environmentally-friendly foamer composition was tested, and the test results can be seen in Tables 1-3, wherein the boiling point of the low-carbon environmentally-friendly foamer composition was 18.8° C. at the pressure of 101.3 KPa.

Embodiment 7

750 g of HFO-1233zd, 249 g of HFC-245eb and 1 g of HFC-254ca were mixed in their liquid phase state in a steel cylinder to obtain a low-carbon environmentally-friendly foamer composition; the mass percentage of HFO-1233zd was 75%; the mass percentage of HFC-245eb was 24.9%; and the mass percentage of HFC-254ca was 0.1%. The performance of the low-carbon environmentally-friendly foamer composition was tested, and the test results can be seen in Tables 1-3, wherein the boiling point of the low-carbon environmentally-friendly foamer composition was 18.6° C. at the pressure of 101.3 KPa.

The features and effects of this invention are described through comparing the performance of the low-carbon environmentally-friendly foamer compositions obtained in Embodiments 1-7 with the performance of HFC-245fa and cyclopentane. The results can be seen in Tables 1-3. Wherein:

Determination of the heat conductivity coefficient is subject to the GB10295-88.

Determination of the energy consumption is subject to GB/T8059.3-1995.

Determination of the boiling point: The boiling point was determined by using an automatic comparison boiling point determination meter.

TABLE 1

Comparison of the environmental performance of foamer

| Medium | ODP | GWP |
| --- | --- | --- |
| Embodiment 1 | 0 | 117 |
| Embodiment 2 | 0 | 4 |
| Embodiment 3 | 0 | 88 |
| Embodiment 4 | 0 | 59 |
| Embodiment 5 | 0 | 45 |
| Embodiment 6 | 0 | 30 |
| Embodiment 7 | 0 | 74 |
| HFC-245eb | 0 | 290 |
| HFO-1233zd | 0 | 1 |
| HFC-254ca | 0 | 190 |

Table 1 lists the environmental performance of the environmentally-friendly foamer compositions obtained in embodiments 1-7. From Table 1, it can be seen that the ODPs of the environmentally-friendly foamer compositions obtained in Embodiments 1-7 are 0, which means no destructive effect on the atmospheric ozone layer; and the GWPs are all smaller than the GWP of HFC-245fa (790).

TABLE 2

Comparison of the heat conductivity coefficient of foamer

| Medium | Heat conductivity coefficient reduction % (Compared with an HFC-245fa system) | Heat conductivity coefficient reduction % (Compared with a cyclopentane system) | Heat conductivity coefficient reduction % (Compared with the mixture of HFO-1233zd and HFC-245eb, without HFC-254ca) |
| --- | --- | --- | --- |
| Embodiment 1 | 42.8 | 25.9 | 15.9 |
| Embodiment 2 | 12.5 | 11.4 | 1.4 |
| Embodiment 3 | 41.5 | 22.6 | 12.6 |
| Embodiment 4 | 35.9 | 16.4 | 6.4 |
| Embodiment 5 | 29.6 | 12.9 | 2.9 |
| Embodiment 6 | 22.7 | 9.4 | 0.4 |
| Embodiment 7 | 37.6 | 17.9 | 7.9 |

Table 2 lists the heat conductivity coefficients of the environmentally-friendly foamer compositions obtained in Embodiments 1-7. From Table 2, it can be seen that compared with the HFC-245fa system, the cyclopentane system, and the HFC-254ca-free system of the mixture of HFO-1233zd and HFC-245eb in a ratio of 1:1, the heat conductivity coefficients of the environmentally-friendly foamer compositions obtained in Embodiments 1-7 are greatly reduced.

TABLE 3

Comparison of the energy consumption of the foamer

| Medium | Energy consumption reduction % (Compared with the HFC-245fa system) | Energy consumption reduction % (Compared with cyclopentane system) | Energy consumption reduction % (Compared with the HFC-254ca-free system of the mixture of HFO-1233zd and HFC-245eb in a ratio of 1:1) |
|---|---|---|---|
| Embodiment 1 | 32.3 | 50.2 | 20.2 |
| Embodiment 2 | 13.8 | 14 | 8.9 |
| Embodiment 3 | 29.1 | 44.8 | 24.8 |
| Embodiment 4 | 23.8 | 38.7 | 18.7 |
| Embodiment 5 | 20.3 | 31.4 | 11.4 |
| Embodiment 6 | 15.8 | 27.6 | 17.6 |
| Embodiment 7 | 25.9 | 42 | 22 |

Table 3 lists the overall energy consumption of refrigerators when the environmentally-friendly foamer compositions obtained in Embodiments 1-7 were applied to refrigerators. From Table 3, it can be seen that compared with the HFC-245fa system, the cyclopentane system, and the HFC-254ca-free system of the mixture of HFO-1233zd and HFC-245eb in a ratio of 1:1, the overall energy consumption of the refrigerators using the environmentally-friendly foamer compositions obtained in Embodiments 1-7 was greatly reduced, and the refrigerators had very low energy consumption.

What is claimed is:

1. A low-carbon environment-friendly foamer composition, comprising the following ingredients in mass percentage:

| | |
|---|---|
| 1-chloro-3,3,3-trifluoropropene | 60-98.99% |
| 1,1,1,2,3-pentafluoropropane | 1-39.9% |
| 1,2,2,3-tetrafluoropropane | 0.01-1%. |

2. The low-carbon environment-friendly foamer composition of claim 1, comprising the following ingredients in mass percentage:

| | |
|---|---|
| 1-chloro-3,3,3-trifluoropropene | 69.99-94.99% |
| 1,1,1,2,3-pentafluoropropane | 5-30% |
| 1,2,2,3-tetrafluoropropane | 0.01-1%. |

3. The low-carbon environment-friendly foamer composition of claim 1, comprising the following ingredients in mass percentage:

| | |
|---|---|
| 1-chloro-3,3,3-trifluoropropene | 80-89.99% |
| 1,1,1,2,3-pentafluoropropane | 10-19.9% |
| 1,2,2,3-tetrafluoropropane | 0.01-1%. |

4. The low-carbon environment-friendly foamer composition of claim 1, comprising the following ingredients in mass percentage:

| | |
|---|---|
| 1-chloro-3,3,3-trifluoropropene | 85-89.99% |
| 1,1,1,2,3-pentafluoropropane | 10-14.99% |
| 1,2,2,3-tetrafluoropropane | 0.01-1%. |

5. The low-carbon environment-friendly foamer composition of claim 1, wherein the composition has a boiling point of 18-19° C. at 101.3 KPa.

6. A preparation method for the low-carbon environmentally-friendly foamer composition of claim 1, wherein all ingredients are physically mixed by mass percentage in a liquid-phase state.

7. A preparation method for the low-carbon environmentally-friendly foamer composition of claim 2, wherein all ingredients are physically mixed by mass percentage in a liquid-phase state.

8. A preparation method for the low-carbon environmentally-friendly foamer composition of claim 3, wherein all ingredients are physically mixed by mass percentage in a liquid-phase state.

9. A preparation method for the low-carbon environmentally-friendly foamer composition of claim 4, wherein all ingredients are physically mixed by mass percentage in a liquid-phase state.

10. A preparation method for the low-carbon environmentally-friendly foamer composition of claim 5, wherein all ingredients are physically mixed by mass percentage in a liquid-phase state.

* * * * *